US012642702B2

(12) United States Patent
Kinast

(10) Patent No.: US 12,642,702 B2
(45) Date of Patent: Jun. 2, 2026

(54) DEVICE FOR STEADYING THE NON-OPERATIVE EYE DURING EYE SURGERY

(71) Applicant: Robert M. Kinast, Portland, OR (US)

(72) Inventor: Robert M. Kinast, Portland, OR (US)

( * ) Notice: Subject to any disclaimer, the term of this patent is extended or adjusted under 35 U.S.C. 154(b) by 650 days.

(21) Appl. No.: 18/106,412

(22) Filed: Feb. 6, 2023

(65) Prior Publication Data

US 2023/0248575 A1     Aug. 10, 2023

Related U.S. Application Data

(60) Provisional application No. 63/267,691, filed on Feb. 8, 2022.

(51) Int. Cl.
*A61F 9/02* (2006.01)

(52) U.S. Cl.
CPC .............. *A61F 9/029* (2013.01); *A61F 9/026* (2013.01)

(58) Field of Classification Search
USPC ........ 359/647, 448, 450, 646; 351/209, 211, 351/245, 159.78, 178
See application file for complete search history.

(56) References Cited

U.S. PATENT DOCUMENTS

| | | | | |
|---|---|---|---|---|
| 6,869,427 B1 * | 3/2005 | Shokoohi | ................ | A61F 9/007 606/1 |
| 2005/0179866 A1 * | 8/2005 | Biscardi | ................. | A61F 9/007 351/211 |
| 2008/0122736 A1 * | 5/2008 | Ronzani | ............. | G02B 27/0176 345/8 |

FOREIGN PATENT DOCUMENTS

WO      WO-2009103491 A1 *  8/2009  ............... A61B 3/14

* cited by examiner

*Primary Examiner* — Thomas K Pham
*Assistant Examiner* — Jennifer A Jones
(74) *Attorney, Agent, or Firm* — Klarquist Sparkman, LLP

(57) ABSTRACT

A method for eye surgery on an operative eye of an eye surgery patient can comprise a step of securing a monocular device over a non-operative eye of the patient. The monocular device can comprise a frame configured to engage a portion of the patient's face surrounding the non-operative eye and a visual target projector attached to the housing and disposed over the non-operative eye, wherein the monocular device does not cover the operative eye of the patient. The visual target projector can be configured to generate a visual target on which the non-operative eye focuses during eye surgery.

15 Claims, 12 Drawing Sheets

100

105

110

115

100

105

110

130

125

120

200

300

315

310

305

325

320

330

400

405

410

1000

1005

DEVICE FOR STEADYING THE NON-OPERATIVE EYE DURING EYE SURGERY

CROSS REFERENCE TO RELATED APPLICATION

This application claims the benefit of U.S. Provisional Patent Application No. 63/267,691, filed Feb. 8, 2022. The prior application is incorporated herein by reference in its entirety.

FIELD

The present invention generally relates to devices for eye surgery and eye safety, and more particular to devices that provide stimulation to a non-operative eye.

SUMMARY

A method for eye surgery in accordance with certain examples of the invention can solve one or more deficiencies in the prior art. In particular, the method is configured to keep an operative eye open, steady, and/or straight during eye surgery by providing a visual target for a corresponding non-operative eye to focus on during the surgery.

In a representative example, a method for performing an eye surgery can comprise a step of securing a monocular device over a non-operative eye of an eye surgery patient. The monocular device can comprise a housing configured to rest on a portion of a face of the patient surrounding the non-operative eye and a visual target projector attached to the housing and disposed over the non-operative eye. The visual target projector can be configured to generate a visual target on which the non-operative eye focuses during eye surgery. The monocular device does not cover the operative eye of the patient. The method can further comprise a step of activating the visual target projector to generate the visual target.

Additionally, a visual target stimulation device in accordance with certain examples of the invention can solve one or more deficiencies in the prior art. In particular, the visual target stimulation device is configured to keep an operative eye open, steady, and/or straight during eye surgery by providing a visual target for a corresponding non-operative eye to focus on during the surgery.

In a representative example, a visual target stimulation device can comprise (a) a housing component that can house other components of the visual target stimulation device and can also protect the non-operative eye and partially or completely cover the non-operative eye and (b) a visual target projector including but not limited to a light, a display, or a screen that can generate a projected, virtual reality, or augmented reality image. The visual target stimulation device can further comprise (c) electronics, including but not limited to a power source, a light, a backlight, a microprocessor, a Wi-Fi and/or Bluetooth transceiver, a virtual reality and/or augmented reality wearable, a retinal projector, and/or a smartglass, (d) a connected earpiece, and/or (e) an eye-tracking sensor.

In another representative example, a visual target stimulation device can comprise a visual target projector, a frame, and a plurality of struts. The visual target projector can be positioned over a non-operative eye of an eye surgery patient, wherein the visual target projector is configured to project a visual target towards the non-operative eye. The frame can be disposed between the visual target projector and the non-operative eye. Each of the upper frame portion can extend from an edge portion of the frame to the visual target projector. The frame does not cover an operative eye of the patient.

In another representative example, a visual target stimulation device can comprise a housing and a visual target projector. The housing can be configured to be secured around a non-operative eye of an eye surgery patient, wherein the housing is configured to cover the non-operative eye. The visual target projector can be mounted to the housing and disposed over the non-operative eye. The visual target projector can be configured to generate a visual target on which the non-operative eye focuses during eye surgery. The visual target can be generated such that the target minimizes movement of the non-operative eye.

In another representative example, a visual target stimulation device can comprise a holographic projector adjacent a non-operative eye of an eye surgery patient. The holographic projector can be configured to generate a visual target for the non-operative eye to focus on during eye surgery.

The housing component can completely cover or partially cover the non-operative eye and attach to the skin around the non-operative eye, like on the forehead, brow, cheek, lateral face, ear, and/or nasal bridge. In another example, the device would attach adjacent to the eye, like on the forehead, brow, cheek, lateral face, and/or nasal bridge or other part of the face, to project or emit the target.

In some examples, the device can include a temple portion that extends to the ipsilateral ear. Some embodiments of the invention would use detachable and replaceable components like to fit an individual's face. In some embodiments of the invention, the housing component would also contain the visual target or contain an aperture or opening to view the visual target. In some embodiments of the invention, the housing component would be a monocular smartglass or virtual reality headset or augmented reality headset.

In some examples, the visual target or stimulus can be a light or lights, a canvas with paint or coloring, a screen, a display, or a projected or virtual image. The visual target could be non-electronic or electronic. The visual target can be stationary or have movement above the non-operative eye. This visual target can take the form of a pleasant aesthetic experience or entertainment, such as light show, video, television program, or movie, which can both help keep the non-operative eye open and steady and help keep the patient at ease and comfortable; if a patient is at ease and comfortable less anesthetic medicine may be required. The visual target can be programmable or non-programmable. The visual target can be streamed (like over WiFi or Bluetooth) or non-streamed. The visual target can be virtual or non-virtual, augmented, or non-augmented. The visual image can use a screen, a projector, or be screenless. The visual image can be projected above or into the eye or onto the retina. In some examples, the visual image can use a curved mirror, waveguide, hologram, or virtual retinal display (also known as a retinal projector or retinal scan display). In some examples, the device could include backlighting, lenses, adjusting mechanisms, dials, spacers, lasers, mirrors, prisms, or other parts. In some examples, the visual target can be accompanied by an optional earpiece with audio information.

In some examples, the other electronics can include but not be limited to a power source such as a battery, a circuit board including a microprocessor, Wi-Fi and/or Bluetooth, virtual reality or augmented reality or retinal projection or smartglass capabilities, a sensor, and/or an earpiece.

In some examples, the device can include a centering mechanism to help position the target in an optimal location.

In some examples, the device can include a sensor to detect if the non-operative eye is open and centered. In some examples, the device can include a feedback mechanism to adjust the target based on the sensor information, like changing a light stimulus or image if the non-operative eye deviates from the target.

In some examples, the device can be reusable and transferable, while in other examples it can be a single-use disposable device.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosure will become more apparent from the following detailed description, claims, and accompanying figures.

DETAILED DESCRIPTION

General Considerations

Figure 1A:
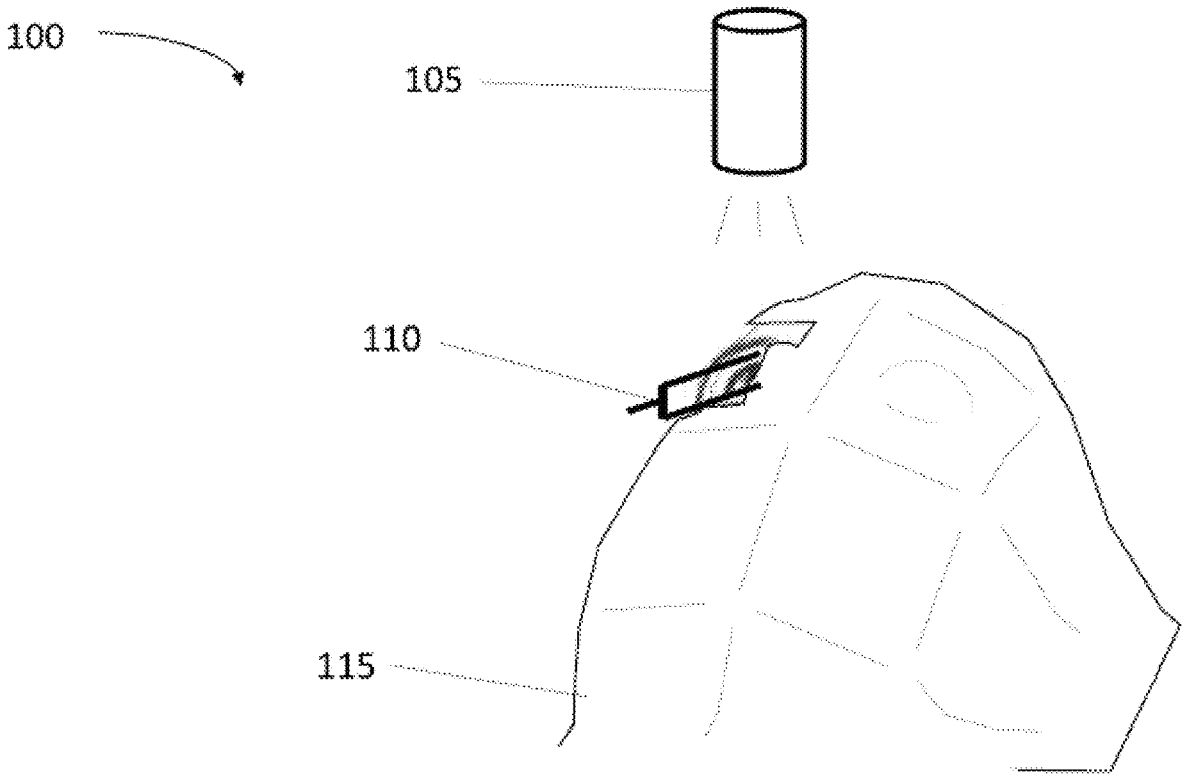
FIG. 1A depicts an oblique view of a patient undergoing an eye surgery on an operative eye.

For purposes of this description, certain aspects, advantages, and novel features of examples of this disclosure are described herein. The disclosed methods, apparatus, and systems should not be construed as being limiting in any way. Instead, the present disclosure is directed toward all novel and nonobvious features and aspects of the various disclosed examples, alone and in various combinations and sub-combinations with one another. The methods, apparatus, and systems are not limited to any specific aspect or feature or combination thereof, nor do the disclosed examples require that any one or more specific advantages be present or problems be solved.

Although the operations of some of the disclosed examples are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

The term "eye surgery" generally refers to any surgery, procedure, treatment, or operation that benefits from a human eye being steady, open, or forward-facing during the surgery, procedure, treatment, or operation. In some examples, the eye surgery may be performed on the human eye, but in other examples, the eye may be only incidental to the eye surgery. Examples of eye surgeries include but are not limited to cataract removal, LASIK, corneal transplantation, and retinal detachment repair.

As used herein, the term "operative eye" generally refers to the eye undergoing or directly involved with an eye surgery, while the term "non-operative eye" generally refers to the eye not subject to the eye surgery.

As used herein, the term "visual target" generally refers to anything on which the non-operative eye may focus, including, for example, a light or lights, a canvas with paint or coloring, a picture, a photograph, a still digital image, a video, a movie, a television show, a hologram, or a projected or virtual image. The term "visual target projector" generally refers to any device capable of projecting or displaying the visual target to the patient's non-operative eye.

As used herein, the terms "stimulate" or "stimulation" of an eye generally refers to any activity and/or stimuli that cause a single eye of wearer to engage with the activity and/or stimuli in some manner to maintain and/or change a position of the single eye.

As used herein, the term "smartglass" generally refers to a wearable, networkable device capable of projecting a visual target on which a non-operative eye may focus. Examples of "smartglass" include but are not limited to a headset, helmet, monocle, glasses, brace, or other body-mounted device with augmented reality, virtual reality, or holographic capabilities.

As herein, the term "monocular" generally means for use with one eye only. For example, a "monocular smartglass" can refer to a smartglass device that covers only a first eye but leaves a second eye unobstructed such that a surgery, treatment, or procedure can be performed on the second eye.

Overview of the Operating Environment

FIG. 1 depicts an operating environment 100 for eye surgery on an operative eye, according to one example. The operating environment 100 can include a microscope 105, a lid speculum 110, and a drape 115. However, depending on the nature of the eye surgery being performed, other examples of the operating environment 100 can comprise additional or alternative tools, equipment, components, or features.

Eye surgery can be performed under the microscope 105. The microscope 105 can be a device configured to illuminate or magnify the operative eye or portions of the operative eye during the eye surgery. The microscope 105 can alternatively be referred to as an ophthalmic microscope, a surgical microscope, a stereoscopic microscope, or an operating microscope. During the eye surgery, the microscope 105 can be pointed at and/or shine light at the operative eye.

Although some examples of the microscope 105 can be adjusted to align with the operative eye, the microscope 105 will not necessarily magnify or illuminate the patient's operative eye if the operative eye moves, closes, or makes an intraoperative movement during the surgery. Thus, to keep the operative eye steady, patients can stare with the operative eye at a light projected by the microscope 105.

The lid speculum 110, alternatively referred to as an eyelid retractor, can be a device configured to prevent the operative eye from closing during surgery. The lid speculum 110 can be a fixed speculum, an adjustable speculum, or any other suitable kind of lid speculum, eyelid retractor, or related device.

The lid speculum 110 can comprise a lower blade and an upper blade. The lower blade can be inserted under a lower eyelid of the operative eye and the upper blade can be inserted under an upper eyelid of the operative eye. The upper and lower blades of the lid speculum 110 can be wire blades, closed blades, or any other blades suitable for restraining a lower or upper eyelid during surgery.

Although the operative eye is held open by the lid speculum 110, the non-operative eye is not constrained by the lid speculum 110 and can blink freely and can close. This can be problematic since when the non-operative eye closes, the operative eye is more likely to 1) try to close and cause a squeezing force against the lid speculum 110, which can increase eye pressure and make eye surgery more challenging, 2) lead to a Bell's Reflex, where the operative eye turns upward towards the top of the head and under the upper eyelid, which makes the eye surgery more challenging, and 3) wander and become a moving target, which also makes the eye surgery more challenging. However, if the non-operative eye looks straight ahead into space, the operative eye is also usually straight and steady, which makes the eye surgery easier.

The drape 115 can isolate the operative eye, provide a sterile surrounding for the operative eye, and/or protect the non-operative eye during surgery. In some examples, the drape 115 can cover a portion of the patient's body—e.g., a portion or an entirety of the patient's neck, face, and/or the non-operative eye. The drape 115 can leave the patient's operative eye exposed. For example, the drape 115 can have a cut-out for the operative eye.

Overview of the Disclosed Technology

Figure 1B:
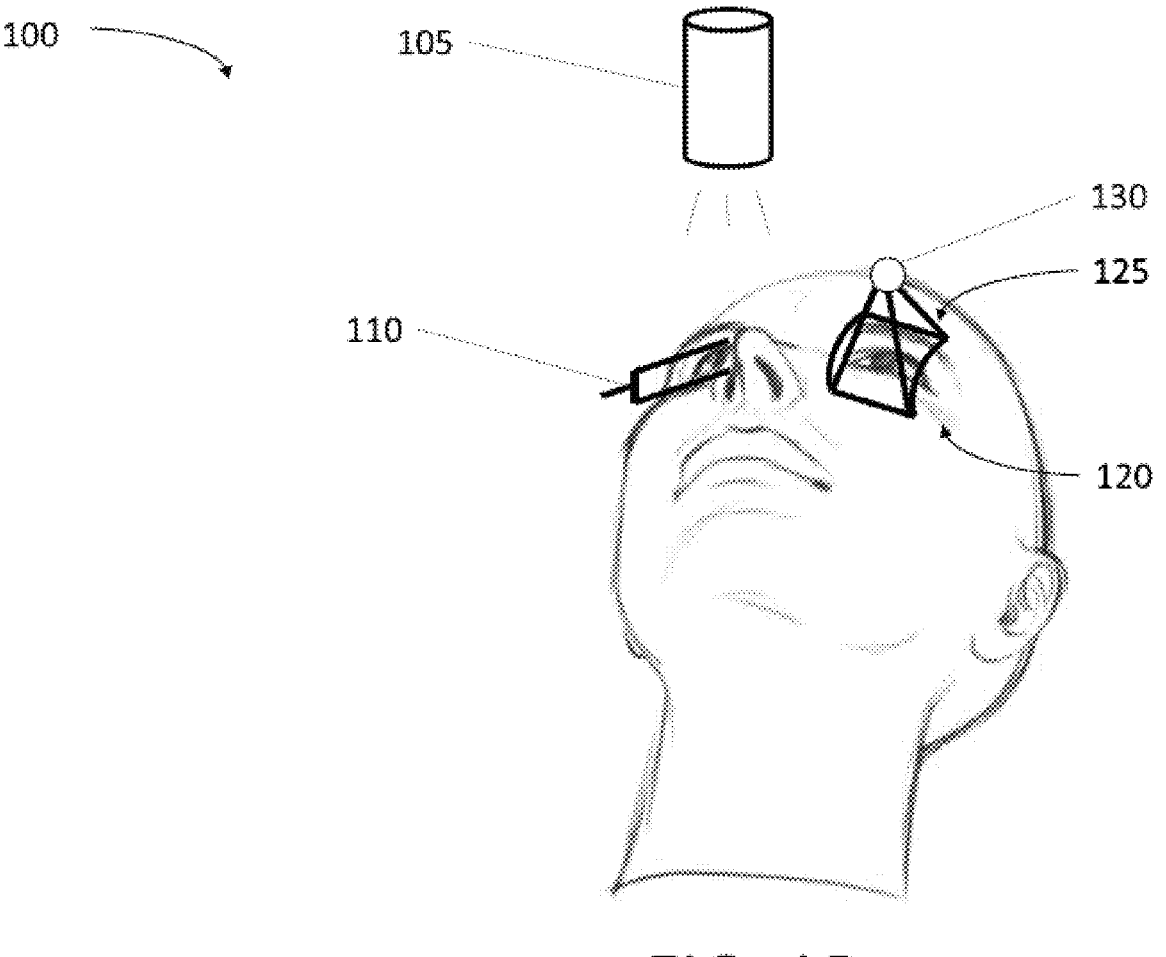
FIG. 1B depicts an oblique view of the patient undergoing eye surgery with a visual target stimulation device covering the patient's non-operative eye.

FIG. 1B depicts the operating environment 100, according to another example. The operating environment 100 of FIG. 1A can further comprise a visual target stimulation device 120. In FIG. 1B, the drape 115 has been removed to better illustrate the visual target stimulation device 120, which can be disposed under the drape 115 that can cover the non-operative eye. However, other operating environments 100 can include both the drape 115 and the visual target stimulation device 120. In some examples, the drape 115 can include a cutout for the visual target stimulation device 120.

The visual target stimulation device 120, which can alternatively be referred to as a monocular device, a monocular, or an eye-steadying device, can be disposed over the non-operative eye. In some examples, the visual target stimulation device 120 is placed under the drape 115 and over the patient's non-operative eye. By covering the non-operative eye, the visual target stimulation device 120 can beneficially protect the non-operative eye during surgery and differentiate the non-operative eye from the operative eye. Furthermore, the visual target stimulation device 120 can beneficially provide a visual target for the non-operative eye to focus on. Focusing on the visual target can help keep the non-operative eye open and/or steady and/or help keep the patient visually engaged and/or entertained during surgery. In summary, keeping the non-operative eye open, steady, or engaged during the surgery can beneficially keep the operative eye similarly open, steady, or engaged.

The visual target stimulation device 120 can comprise a frame 125 and a visual target projector 130. However, other examples of the visual target stimulation device 120 can comprise additional or alternative components.

The frame 125 can support the visual target projector 130 over the non-operative eye. Thus, the frame 125 can be disposed over the non-operative eye. For example, the frame 125 can be placed over an eye socket of the patient's non-operative eye. However, in other examples, the frame 125 can be adjacent the non-operative eye. For example, the frame 125 can be placed on or secured to an ipsilateral cheek, temple, or ear of the patient. In further examples, the frame 125 can be a headband wrapped around the patient's head.

In some examples, the frame 125 does not need to be attached or secured to the patient's body. Instead, the frame 125 can be a stand or structure adjacent the patient's head. For example, the frame 125 can be a scaffold attached to an operating table, a chair, or the microscope 105 such that the frame 125 positions the visual target projector 130 over the patient's non-operative eye.

The frame 125 can comprise a lower frame portion and an upper frame portion. However, other examples of the frame can comprise additional or alternative components.

The lower frame portion can be chassis or structure disposed over the patient's non-operative eye. In some examples, the lower frame portion can comprise an open wire frame disposed on a portion of the patient's face surrounding the non-operative eye. The lower frame portion can be configured to not substantially obstruct the patient's line-of-sight from the non-operative eye to the visual target. For example, the lower frame portion can have an aperture or apertures disposed between the non-operative eye and the visual target projector 130. In some examples, the lower frame portion serves as a base for the visual target stimulation device 120.

The upper frame portion can connect or couple the lower portion to the visual target projector 130. In some examples, the upper frame portion can be a plurality of wires or struts connecting the lower frame portion to the visual target projector 130. However, in other examples, the upper frame portion can be a solid or opaque structure that reduces the amount of ambient light entering the patient's non-operative eye.

The visual target projector 130 can be a device configured to project or display a visual target to the patient. In the illustrated example, the visual target projector 130 can comprise a light bulb, LED, or other light source. In the illustrated example, the visual target is the light generated or projected by the light bulb, wherein the light is shone into the patient's non-operative eye. However, in other examples, the visual target can be a light or lights, a canvas with paint or coloring, a picture, a photograph, a still digital image, a video, a movie, a television show, a hologram, or a projected or virtual image. In these other examples, the visual target projector 130 can be any device capable of projecting or displaying the visual target to the patient's non-operative eye, including a light bulb, a screen, a retinal projector, a holographic projector, an augmented reality display, or a virtual reality display.

The visual target stimulation device 120 or the visual target projector 130 can further comprise components to power or control the visual target projector 130. In some examples, the visual target stimulation device 120 can further comprise a battery, a wireless charger, or a wired power source for powering the visual target projector 130 or other electrical components of the visual target stimulation device 120. In some examples, the visual target stimulation device 120 can comprise a switch, a dial, a button, a processor, a wireless transceiver (e.g., a Bluetooth or Wi-Fi transceiver), or a wired connection (e.g., a USB port) to activate or otherwise control the visual target projector 130.

In some examples, the visual target stimulation device 120 can further comprise components for securing the visual target stimulation device 120 to the patient. For example, the visual target stimulation device 120 can further comprise straps, adhesive, tape, or other attachment mechanisms to ensure that the visual target stimulation device 120 does not shift or move relative to the patient's non-operative eye during the eye surgery.

In some examples, the visual target stimulation device 120 can further comprise components for reducing discomfort caused by the visual target stimulation device 120. For example, the visual target stimulation device 120 can further comprise padding, cushions, rests, insulation, or other supports disposed at locations where the visual target stimulation device 120 contacts the patient's face or head.

Example Methods of Using the Disclosed Technology

A method for performing eye surgery on the patient's operative eye can first comprise a step of placing the visual target stimulation device 120 over the patient's non-operative eye. In some examples, the visual target stimulation device 120 can be substituted for one or more visual target stimulation devices disclosed elsewhere in this application.

In some examples, the visual target stimulation device 120 can be securely fastened relative to the non-operative eye during eye surgery. This can beneficially prevent the visual target stimulation device 120 from becoming misaligned during the eye surgery. Thus, some examples of the visual target stimulation device 120 can further comprise tape, straps, adhesive, or other mechanisms that securely fasten the visual target stimulation device 120 to the patient.

Next, in some examples, the method comprises a step of calibrating the visual target stimulation device 120. In some examples, the size, brightness, clarity, position, or orientation of the visual target can be calibrated. In some examples, the physical position or orientation of the visual target projector 130 can be adjusted to calibrate the visual target stimulation device 120. In some examples, the visual target can be calibrated by adjusting one or more lenses disposed between the visual target projector 130 and the non-operative eye.

In some examples, in which the visual target comprises an entertainment program such as a movie, video, or television show, the calibration step can additionally or alternatively comprise selecting which entertainment program is used as the visual target. This step can optionally comprise the step of downloading the entertainment program to an on-board memory of the visual target stimulation device 120 or generating a request to stream the entertainment program to the visual target stimulation device 120.

Next, the method can comprise a step of activating the visual target stimulation device 120 to project the visual target towards the patient's non-operative eye. In some examples, the visual target can be a light or lights, a canvas with paint or coloring, a picture, a photograph, a still digital image, a video, a movie, a television show, a hologram, or a projected or virtual image. In some examples, the visual target can be activated in response to a command from a processor, computer, or microcontroller. In some of these examples, the command can be received over a wired or wireless connection. In some examples, the visual target can be activated in response to a command input via a button, dial, switch, or keypad on the visual target stimulation device 120.

Next, the method can comprise a step of projecting the visual target towards the patient's non-operative eye.

Next, in some examples, the method can comprise a step of adjusting the visual target. In some examples, the adjustment can be in response to one or more received commands. In some examples, the commands can be analog commands (e.g., transmitted through a button, dial, or switch built into the visual target stimulation device 120) input by a surgeon or another user. In other examples, the commands can be digital (e.g., received by a processor or other electronic device of the visual target stimulation device 120). In these embodiments, the commands may be received from a sensor on the visual target stimulation device 120 (e.g., an eye-tracking sensor or other biometric sensor), received from an interface on the visual target stimulation device 120, or received over a wired or wireless connection from an external device.

In some examples, the adjustment can be in response to one or more received commands generated by an eye-tracking sensor on the visual target stimulation device 120. The received commands can signify a determination by the eye-tracking sensor that the patient's non-operative eye has moved or is no longer centered or focused on the visual target. In some examples, the visual target stimulation device 120 can determine that the patient's non-operative eye is no longer open, centered, or focused based on any of a position, movement, orientation, or an image or series of images of the patient's non-operative eye.

Next, in some examples, the method can comprise a step of adjusting the visual target stimulation device 120 in response to the received commands. In some examples, the adjustment can change which visual target is displayed by the visual target stimulation device 120. In some examples, the adjustment can change the brightness, size, position, orientation, or clarity of the visual target.

In some examples, in which the visual target stimulation device 120 comprises a lens, the adjustment step can comprise adjusting the lens.

In some examples, in which the visual target is an entertainment program, the adjustment can change which entertainment program is used as the visual target.

In some examples, in which the visual target is synced with audio, the adjustment can adjust the volume of the synced audio or change which audio is playing.

Examples of the Disclosed Technology

Figure 2:
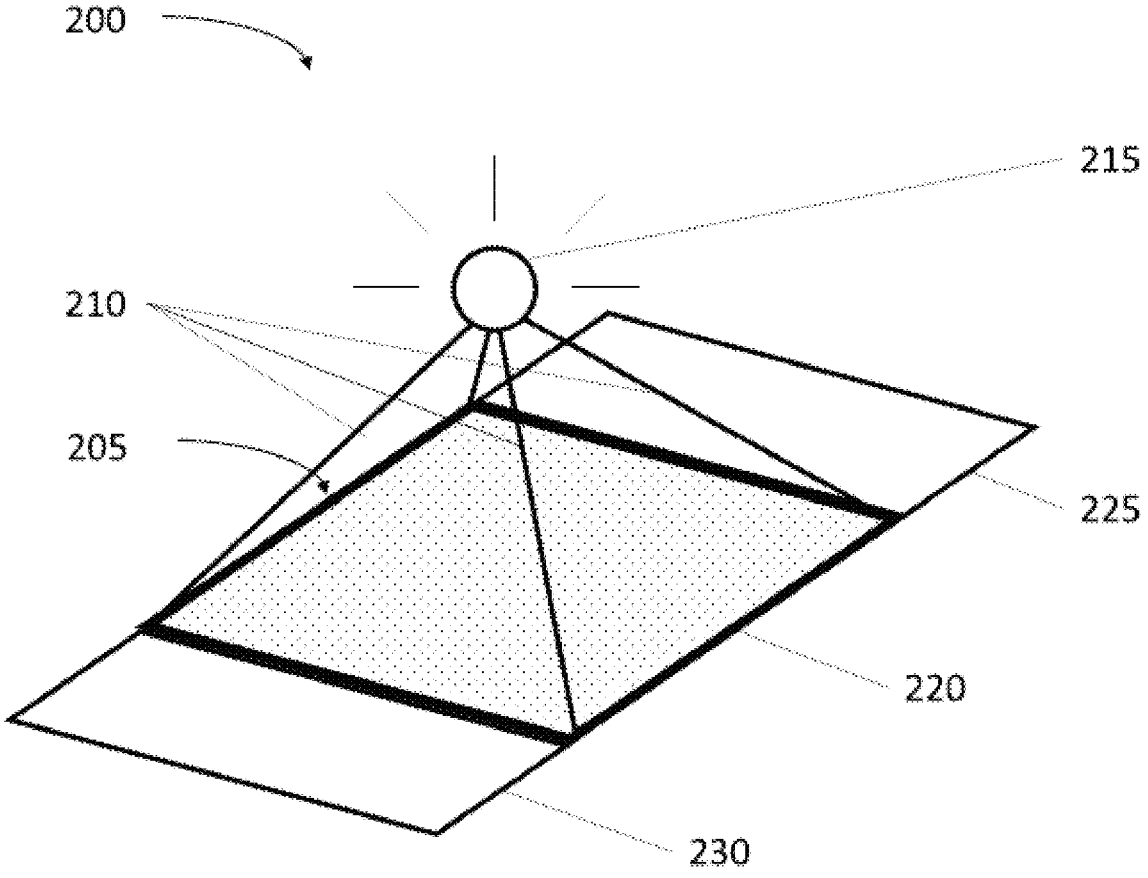
FIG. 2 depicts an oblique view of an open-frame visual target stimulation device, according to one example.

FIG. 2 illustrates an exemplary open-frame visual target stimulation device 200. The visual target stimulation device 200 can include a lower frame portion 205, an upper frame portion 210, a visual target projector 215, an eye shield 220, a forehead rest, and a cheek rest. However, other examples of the visual target stimulation device 200 can comprise additional or alternative components.

The lower frame portion 205 can serve as a chassis or a base for the visual target stimulation device 200. In the illustrated example, the lower frame portion 205 can comprise a quadrilateral frame outlining a perimeter of the non-operative eye. The quadrilateral frame can comprise bars, tubes, plates, blocks, or any other suitable structural component instead of a wire frame. However, other examples of the lower frame portion 205 can form different shapes or geometries rather than that of a quadrilateral frame.

The lower frame portion 205 can be configured to not substantially obstruct a patient's view of the visual target or visual target projector 215. For example, the lower frame portion 205 can be designed such that no frame elements cross over the non-operative eye. In other examples, the lower frame portion 205 can comprise an aperture or apertures formed over the non-operative eye.

In the illustrated example, the lower frame portion 205 can be substantially planar. However, in other examples, the lower frame portion 205 can have alternative geometries. In other examples, the lower frame portion 205 can substantially conform to the topography of a portion of the patient's face. For example, the lower frame portion 205 can conform to a portion of the patient's face surrounding the non-operative eye.

The lower frame portion 205 can be formed of plastic, metal, silicone, glass, or any suitable durable material.

In some examples, the lower frame portion 205 can be placed on a portion of an eye socket surrounding the non-operative eye. In other examples, the lower frame portion 205 can be placed on a forehead, cheek, temple, or ear of the patient. In some examples, the lower frame portion 205 can be placed on an ipsilateral cheek, temple, or ear on the same side of the patient's face as the non-operative eye.

In some examples, the lower frame portion 205 can come in a variety of premade or custom sizes configured to fit a variety of patients with different facial sizes and/or geometries. In some of these examples, the lower frame portion 205 can be custom-made to promote a better fit of the visual target stimulation device 200. For example, the lower frame portion 205 can be 3D-printed to fit a specific patient's facial structure. In some of these examples, the lower frame portion 205 can detach from the rest of the visual target stimulation device 200 to allow the visual target stimulation device 200 to be configured with different lower frame portions 205.

In some examples, the lower frame portion 205 is configured to be placed over either a patient's left eye or a patient's right eye. In other examples, the lower frame portion 205 can be placed over either the left eye or the right eye.

The upper frame portion 210 be configured to at least partially cover the non-operative eye during eye surgery. Covering the non-operative eye can beneficially prevent a surgeon from operating on the incorrect eye and/or prevent the surgeon from accidently pressing his or her fingers, hand, or wrist into the non-operative eye. Furthermore, the upper frame portion 210 couples the visual target projector 215 to the lower frame portion 205.

The upper frame portion 210 can comprise a plurality of struts, wires, blocks, tubes, or any other suitable structural components. In the illustrated example, the upper frame portion 210 can comprise four structural members, but other examples of the upper frame portion 210 can comprise different numbers of structural members. In the illustrated example, each structural member can extend from a corner portion of the lower frame portion 205 and converge at the visual target projector 215. However, the structural members can extend from any portion of the lower frame portion 205, including but not limited to edge portions, intermediate portions, or central portions.

In some examples, the upper frame portion 210 can have an open-frame design, wherein the open-frame upper frame portion 2 one or more apertures between the structural members. In the illustrated example, the upper frame portion 210 comprises triangular-shaped apertures, wherein two sides of the triangular-shaped apertures are formed by the structural members and a third side is formed by an edge portion of the lower frame portion 205.

The upper frame portion 210 can be formed of plastic, metal, silicone, glass, or any suitable durable material. In some examples, the upper frame portion 210 can be formed from the same material as the lower frame portion 205.

In some examples, the upper frame portion 210 can be adjusted to vary the distance between the non-operative eye and the visual target projector 215. For example, the upper frame portion 210 can comprise collapsible, foldable, telescoping, or extendable structural members that allow the distance between the visual target projector 215 and the patient's non-operative eye to be adjusted. In these examples, the upper frame portion 210 can further comprise latches, locking members, or other components to fix the length of the upper frame portion 210. In these examples, the upper frame portion 210 can further comprise motors, actuator, or other components to extend or contract the upper frame portion 210. The upper frame portion 210 can further comprise buttons, dials, sliders, or switches that control the extension, contraction, or change in length of the upper frame portion 210.

The visual target projector 215 can project or display a visual target on which the patient's non-operative eye can focus. Providing the visual target for the patient's non-operative eye to focus on can help keep the non-operative eye open and steady during surgery, which in turn beneficially steadies the operative eye. Furthermore, in some examples, the visual target can take the form of a pleasant aesthetic experience or entertainment, which can beneficially keep the patient at ease and thereby reduce the amount of anesthetic medicine required during the eye surgery.

In the illustrated embodiment, the visual target projector 215 can comprise one or more light bulbs—including but not limited to LEDs, halogen bulbs, fluorescent bulbs, or incandescent bulbs—suspended over the non-operative eye. However, in other examples, the visual target projector can comprise a canvas, a drawing, a mirror, a screen, a display, a smartglass, virtual retinal display, retinal projector, retinal scan display or other suitable interface disposed over the non-operative eye. In some of these examples, the visual target projector 215 can comprise a display output of a monocular virtual reality ("VR") headset, a monocular augmented reality ("AR") headset, a monocular set of smart glasses, or any other suitable wearable technology device.

In the illustrated example, the visual target projector 215 comprises a single light bulb that projects a single light as the visual target. In some of these examples, the single light bulb can flash or be arranged to form a pattern of flashes or a light show. In some examples, the light bulb can be colored or change color.

In some examples, the visual target projector 215 can comprise a static visual target—including but not limited to a drawing, a canvas, or a photograph—that is illuminated by the one or more light bulbs.

In some examples, the lights can be arranged to form a display screen. The display screen can show a static image—including but not limited to a picture, silhouette, or reflection—on which the patient can focus. In some examples, the display screen can show a movie, video clip, or light show on which the patient can focus.

In some examples, the visual target projector 215 can comprise components or features configured to adjust the position of the visual target relative to the non-operative eye. For example, the visual target projector 215 can comprise one or more actuators, tracks, pivots, or motors that physically adjust the distance, position, or orientation between the visual target projector 215 and the patient's non-operative eye. In other examples, the visual target projector 215 can be perceived to adjust the distance, position, or orientation between the visual target projector 215 and the patient's non-operative eye, for example, by digitally manipulating the appearance of the visual target. In other examples, the visual target projector 215 adjusts the visual target using one or more lenses disposed between the visual target projector 215 and the non-operative eye.

In some examples, the visual target projector 215 can be detached from the frame 205 and/or the upper frame portion 210. This can beneficially different kinds of visual target projectors 215 to be used on the visual target stimulation device 200. Additionally or alternatively, configuring the visual target projector 215 to be detachable beneficially allows other components of the visual target stimulation device 200 to be sterilized or disposed of between eye surgeries without also disposing of the visual target projector 215.

Some examples of the visual target projector 215 can further comprise buttons, dials, sliders, keypads, joysticks, or touchpads that allow a surgeon or user to control the distance, position, or orientation of the visual target projector 215. In other examples, the distance, position, or orientation of the visual target projector 215 can be automatically adjusted by a computer, processor, controller, or other electronics that can either be mounted to the visual target stimulation device 200 or be in wired or wireless communicative contact with the visual target stimulation device 200 (e.g., via a Wi-Fi, Bluetooth, or radio connection).

The visual target stimulation device 200 can further comprise an eye shield 220 that can beneficially prevent a surgeon from accidently pressing their fingers, hand, or wrist onto the non-operative eye during the eye surgery and can protect the eye from falling or errant objects. The eye shield 220 can be disposed between the visual target projector 215 and the non-operative eye. In some examples, the eye shield 220 is secured or attached to the lower frame portion 205 at one or more locations. In the illustrated example, the eye shield 220 is disposed in a central aperture of the lower frame portion 205.

In one example, the eye shield 220 can comprise a plate with one or more apertures. The apertures can be disposed on the plate such that the eye shield 220 does not obscure the patient's view of the visual target. In some examples, the eye shield 220 covers the entirety of the non-operative eye. In some examples, the eye shield 220 can be flush against the non-operative eye or against a portion of the patient's face surrounding the non-operative eye. In other examples, the eye shield 220 can be substantially planar. However, other examples of the eye shield 220 may have different geometries.

The visual target stimulation device 200 can further comprise one or more rests. The illustrated example depicts the forehead rest 225 and the cheek rest 230 for interfacing the visual target stimulation device 200 with a patient's forehead and cheek, respectively. In some of these examples, the forehead rest 225 and the cheek rest 230 are only placed at locations at which the patient's face or body contacts the visual target stimulation device 200. In other examples, the visual target stimulation device 200 can comprise alternative or additional rests, pads, cushions, or supports that allow the visual target stimulation device 200 to rest on a patient's brow, lateral face, ear, and/or nasal bridge or other part of the patient's face. In some examples, the forehead rest 225 and the cheek rest 230 are integrated with the lower frame portion 205. In other examples, the forehead rest 225 and the cheek rest 230 are not part of the lower frame portion 205 but are still attached to the lower frame portion 205.

The forehead rest 225 and the cheek rest 230 can be formed of plastic, cloth, fabric, metal, silicone, glass, or any suitable durable material.

In some examples, the forehead rest 225 and the cheek rest 230 can comprise padding, insulation, or cushioning. The padding, insulation, or cushioning can beneficially reduce discomfort caused by the visual target stimulation device 200.

In some examples, the forehead rest and the cheek rest can further comprise straps, tape, adhesive, or other attachment mechanisms for securing the rests to the patient's face. The attachment mechanisms can beneficially prevent the visual target stimulation device 200 from becoming misaligned or from shifting relative to the non-operative eye during the eye surgery.

In some examples, the forehead rest 225, the cheek rest 230, and/or any other rests that contact the patient's face can be removable or detachable. If the forehead rest 225, the cheek rest 230, or the other rests are detachable, they can be sterilized or disposed of between eye surgeries. Additionally or alternatively, the detachable forehead rest 225, cheek rest 230, and the other rests can come in a variety of premade or custom sizes configured to fit a variety of patients with different facial sizes and/or geometries, which can beneficially increase patient comfort when the visual target stimulation device 200 is secured to the patient's face. In some of these examples, the forehead rest 225, the cheek rest 230, and the other supports can be custom-made to fit the patient's face, thereby promoting a better fit of the visual target stimulation device 200. In some of these examples, the custom-made forehead rest 225, cheek rest 230, and other supports can be 3D-printed.

Figure 3:
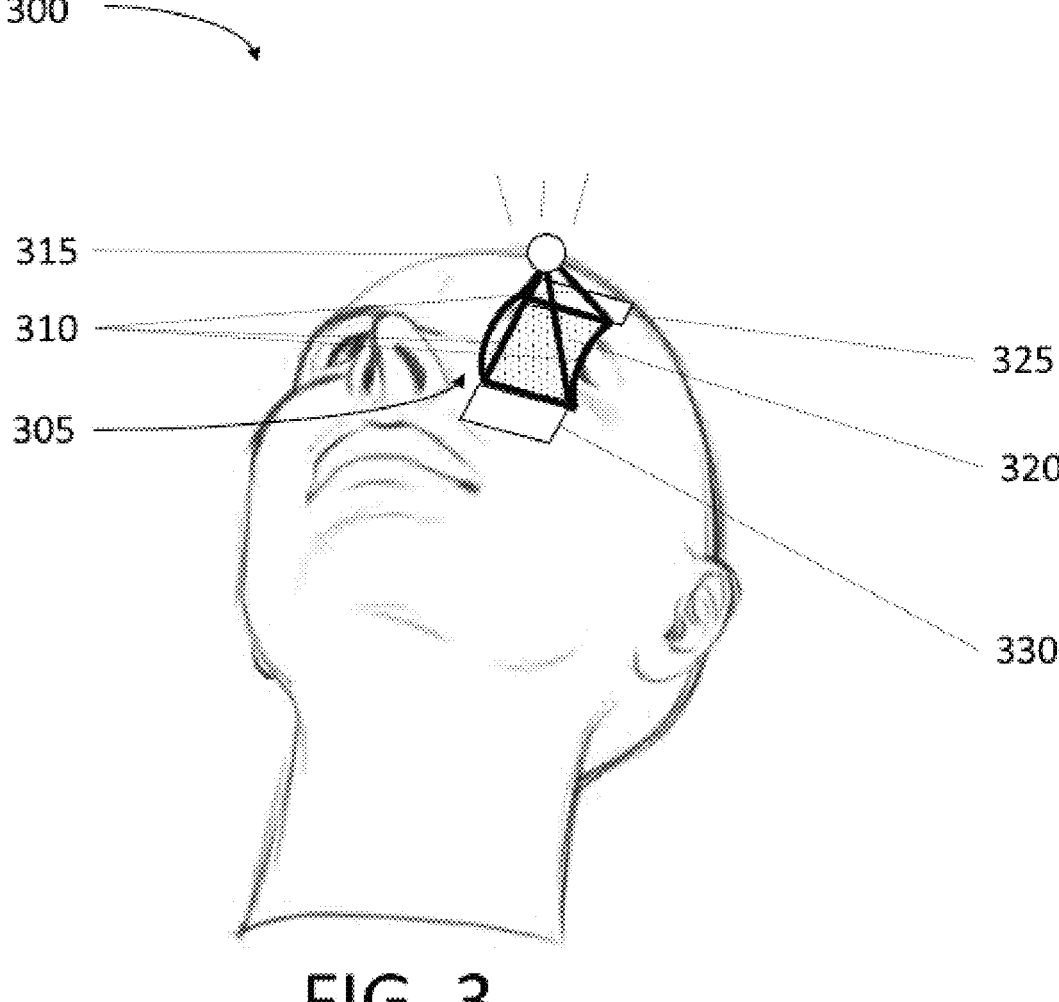
FIG. 3 depicts an oblique view of the open-frame visual target stimulation device of FIG. 2 covering a patient's non-operative eye.

FIG. 3 illustrates a perspective view of an example open-frame visual target stimulation device 300, according to one example. In the illustrated example, the visual target stimulation device 300 is placed over the patient's non-operative eye during eye surgery. In some examples, the visual target stimulation device 300 illustrated in FIG. 3 can be similar to the visual target stimulation device 200 illustrated in FIG. 2.

The open-frame visual target stimulation device 300 can comprise a lower frame 305, an upper frame 310, a visual target projector 315, an eye shield 320, a forehead rest 325, and a cheek rest 330. In some examples, the forehead rest 325 can rest on a frontal bone or forehead region of the patient's head when the visual target stimulation device 300 is placed over the patient's non-operative eye. The cheek rest 330 can rest on a zygomatic bone or cheekbone region of the patient's head when the visual target stimulation device 300 is placed over the patient's non-operative eye. In some embodiments, the lower frame 305 does not directly contact the patient's head.

Figure 4A:
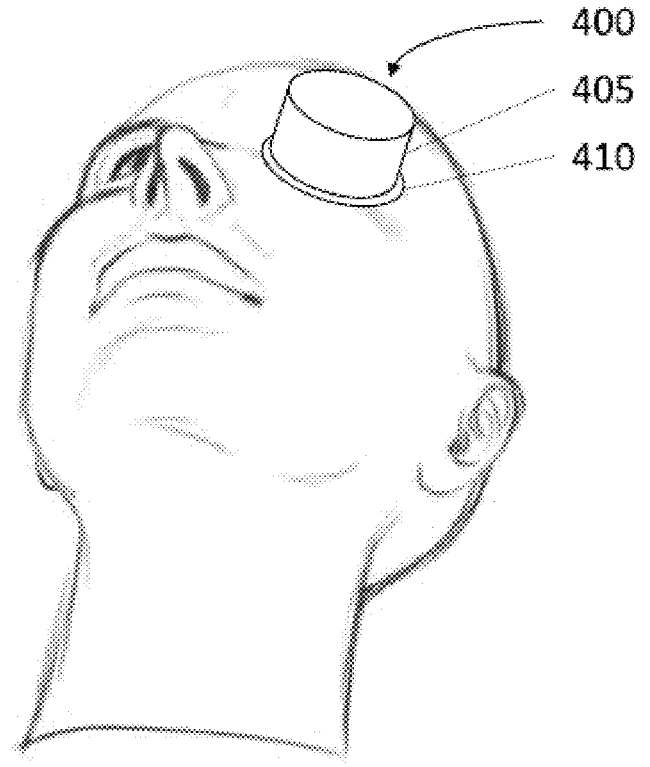
FIG. 4A depicts an oblique view of a closed-frame visual target stimulation device covering a patient's non-operative eye, according to one example.

FIG. 4A illustrates a perspective view of an exemplary closed-frame visual target stimulation device 400, according to one example. In the illustrated example, the visual target stimulation device 400 is placed over the patient's non-operative eye. The visual target stimulation device 400 can comprise a housing component 405 and a cheek rest 410. However, other examples of the visual target stimulation device 400 can comprise additional or alternative components.

The housing component 405 can be a cylindrical, cup-shaped, dome-shaped, or conical housing placed over the patient's non-operative eye. The housing component 405 can alternatively be referred to as a housing or a frame.

The housing component 405 can serve as a chassis or frame for other components of the visual target stimulation device 400. Additionally, by providing a barrier in front of the non-operative eye, the housing component 405 can beneficially prevent a surgeon from accidently pressing their fingers, hand, or wrist onto the non-operative eye during the eye surgery and can protect the eye from falling or errant objects. Furthermore, by prominently covering the non-operative eye, the housing component 405 can help distinguish the non-operative eye from the operative eye, thereby preventing wrong-site surgeries. Finally, the housing component 405 can beneficially block ambient light that can oversaturate the visual target or otherwise distract the patient from focusing on the visual target. In some examples, the housing component can serve a similar function or functions as the lower frame portion 205 and/or the upper frame portion 205 of FIG. 2.

The housing component 405 can comprise a dome-shaped structure with an open end adjacent the non-operative eye. However, other examples of the housing component 405 can be cup-shaped or have any other suitable shape. In some examples, the housing component 405 is substantially enclosed such that outside light can only enter through the open end, thereby blocking any outside light that might obscure or distract the patient's view of the visual target. The open end of the housing component 405 can be adjacent the non-operative eye and configured to engage the non-operative eye. The open end can allow the patient to see the interior of the housing component 405 and the visual target. The housing component 405 can be formed of plastic, metal, silicone, glass, or any suitable durable material.

In some examples, the housing component 405 can rest on a portion of the patient's face, including but not limited to the portion of the patient's face surrounding the non-operative eye. In some examples, the housing component 405 can contact the patient's face at one or more locations. For example, the housing component 405 can comprise a rim at the open end, wherein the rim rests on a portion of the patient's face surrounding the non-operative eye.

In some examples, the housing component 405 can be placed over the patient's left eye or the patient's right eye.

In other examples, the housing component 405 can be interchangeably placed over either the left eye or the right eye.

In some examples, the housing component 405 can further comprise one or more rests 410 where the housing component 405 contacts the patient's face, skin, or body. The rests 410 can also beneficially reduce any discomfort caused by the visual target stimulation device 300 by providing padding, insulation, or cushioning adjacent the patient's face. In these examples, the rests 410 can cushion any sharp edges of the housing component 405. In some examples, the rests 410 comprise rubber or plastic padding disposed around the open end of the housing component 405. However, the rests 410 can be formed of rubber, plastic, foam, fabric, cloth, or any other suitable material. The rests 410 can beneficially help secure the housing component 305 to the patient. For example, the rests 410 can frictionally engage the patient's face, skin, or body. In some of these examples, the rests 410 can frictionally engage a portion of the patient's face surrounding the non-operative eye.

In some examples, the housing component 405 and/or the rests 410 form a seal with the portion of the patient's face surrounding the non-operative eye. The seal can beneficially prevent light from distracting or blinding the patient and prevent light from obscuring the patient's view of the visual target. The seal can also beneficially prevent objects or contaminants from entering the patient's non-operative eye during the eye surgery.

Figure 4B:
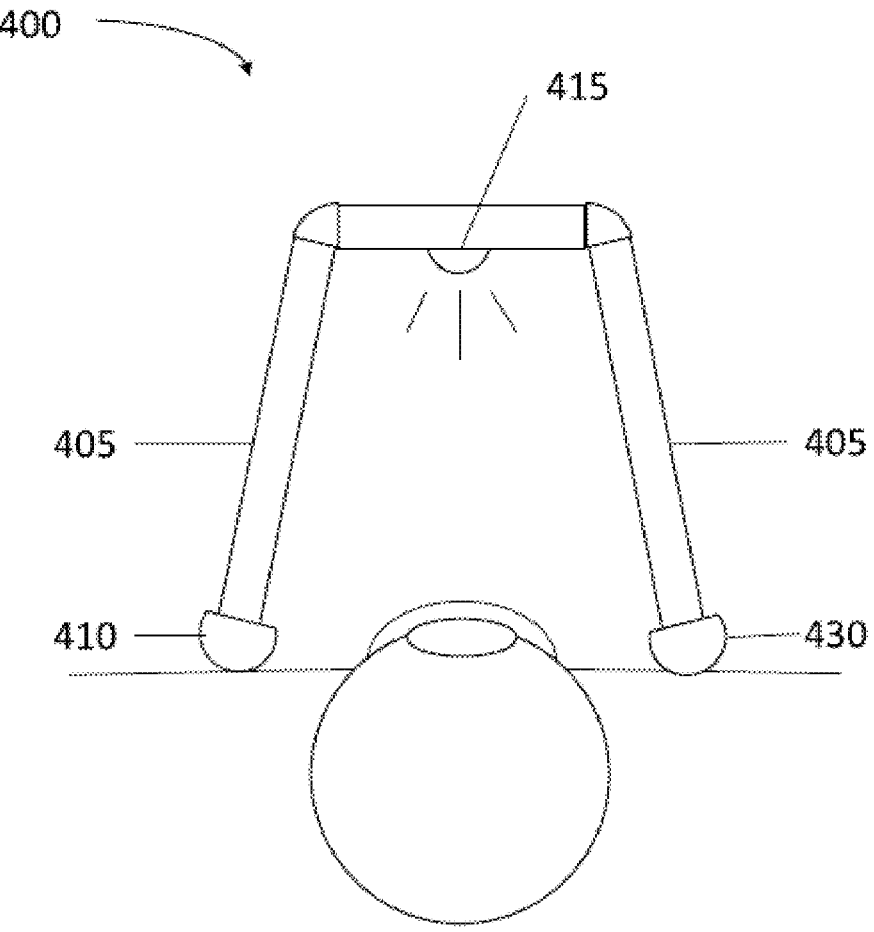
FIG. 4B depicts a cross-section view of the closed-frame visual target stimulation device of FIG. 4A.

FIG. 4B illustrates a cross-sectional view of the visual target stimulation device 400 placed over the patient's non-operative eye, according to one example. The illustrated visual target stimulation device 400 can be similar to the one depicted in FIG. 4A.

The visual target stimulation device 400 can further comprise a light 415. The light 415 can project a visual target on which the patient's non-operative eye can focus. In some examples, the light 415 serves a similar function as the visual target projector 215 depicted in FIGS. 2A-B or the visual target projector 315 depicted in FIG. 3. However, some examples of the light 415 can have different or alternative functions or structures.

In the illustrated example, the light 415 can be disposed on an interior surface of the housing component 405. In some examples, the light 415 can be disposed on an interior surface opposite the open end. In some examples, the light 415 can be disposed on a central portion of the interior surface. In some examples, the light 415 can be disposed on the interior surface such that the light 415 is aligned with the non-operative eye. However, in other examples, the light 415 can be disposed on other surfaces of the housing component 405.

In some examples, the light 415 or the visual target stimulation device 400 can comprise additional components for controlling the light 415, such as a switch, button, dial, controller, processor, or computer for manually or digitally controlling the light 415. In some of these examples, the visual target stimulation device 400 or the light 415 can comprise a wireless transceiver, including but not limited to a Wi-Fi or a Bluetooth transceiver, or a wired transceiver, including but not limited to a USB port, for receiving instructions or data for controlling the light 415. These additional components can be disposed on an interior surface of the housing component 405, an exterior surface of the housing component 405, or integrated with the housing component 405.

Figure 5:
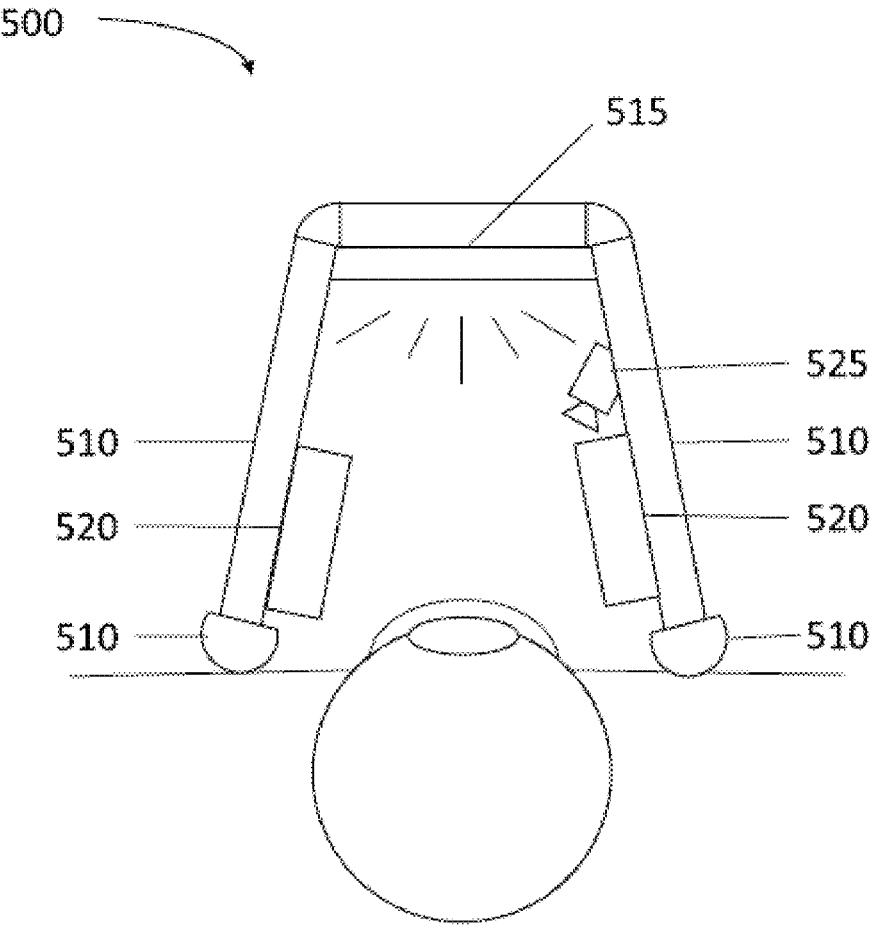
FIG. 5 depicts a cross-section view of a closed-frame visual target stimulation device, according to one example.

FIG. 5 illustrates a cross-sectional view of a visual target stimulation device 500 placed over the patient's non-operative eye, according to another example. The visual target stimulation device 500 can comprise a housing component 505, one or more rests 510, a display screen 515, electronics 520, and an eye tracking sensor 525.

The housing component 505 can comprise a cylindrical, dome-shaped, cup-shaped, or truncated conical structure with an open end adjacent the non-operative eye. The housing component 505 can be configured to fit over the non-operative eye. In some examples, the housing component 505 can have a similar structure and functionality as the housing component 405 illustrated in FIGS. 4A-B.

The rests 510 can be disposed around the open end of the housing component 505. The rests 510 can comprise padding or cushioning to reduce discomfort caused when the visual target stimulation device 500 is placed over the non-operative eye. In some examples, the rests 510 can have a similar structure and functionality as the rests 410 depicted in FIGS. 4A-B.

The display screen 515 can project, display, or show a visual target on which the patient's non-operative eye can focus. The visual target projected by the display screen 515 can be a picture, video clip, light show, or any other suitable target on which the patient's non-operative eye can focus during the eye surgery.

The display screen 515 can be secured to an interior surface of the housing component 05. In some examples, the display screen 515 can be secured to an interior surface of the housing component 505 opposite the open end. However, in other examples, the display screen 515 can be secured to other surfaces of the visual target stimulation device 500. In some examples, the display screen 515 can be disposed on a central portion of the interior surface of the housing component 505 opposite the open end. In some examples, the display screen 515 is disposed on a surface of the housing component 505 such that the display screen 515 is aligned with the non-operative eye. In some examples, the display screen 515 can be integrated into the housing component 505 or be a part of the housing component 505.

In some examples, the visual target projected by the display screen 515 can be adjusted. For example, the size, brightness, clarity, position, or orientation of the visual target can be adjusted to better center or focus the non-operative eye during the eye surgery. Additionally or alternatively, the visual target can be adjusted to keep the non-operative eye during the eye surgery. Thus, some examples of the display screen 515 or the visual target stimulation device 500 can further comprise controls for adjusting or changing the visual target.

In some examples, if the visual target comprises an entertainment program, including but not limited to a video, audio recording, movie, television program, or other form of entertainment, the visual target can be adjusted to play or display a different entertainment program. Thus, some examples of the display screen 515 or the visual target stimulation device 500 can further comprise controls for selecting or changing the entertainment program.

The electronics 520 can further comprise components configured to power the display screen 515, such as a battery, charging cable, or charging port.

The electronics 520 can further comprise components to control the display screen 515. The electronics 520 can comprise a button, switch, dial, keypad, or other interface configured to receive commands. In some examples, the electronics 520 can comprise a controller, processor, or computer for controlling the display screen 515. In some examples, the electronics 520 can comprise a memory for storing instructions and data for controlling the display screen 515. In some of these examples, the electronics 520 can further comprise a transceiver, e.g., a Wi-Fi or a Bluetooth transceiver, for receiving instructions or data for controlling the display screen 515. In some examples, the electronics 520 further comprise a port capable of receiving a wired connection, e.g., a USB port, for receiving digital commands from an external device.

As illustrated, the electronics 520 can be disposed on an interior surface of the housing component 505. The electronics 520 can be disposed on a lateral interior surface of the housing component as to not block the line of sight between the patient's non-operative eye and the display screen 515. However, in other examples, the electronics 520 can be positioned behind the display screen 515 or on an outer surface of the housing component 505 as to similarly not block the patient's view of the display screen 515.

In some examples, the visual target stimulation device 500 optionally includes an eye-tracking sensor 525. The eye-tracking sensor 525 can detect whether the non-operative eye is open, centered, and/or focused on the visual target. In some examples, the eye-tracking sensor 525 can detect one or more movements of the non-operative eye. In some examples, the eye-tracking sensor 525 can detect the position or orientation of the non-operative eye.

In some examples, if the eye-tracking sensor 525 determines that the patient's non-operative eye is not open, centered, or focused on the visual target, the eye-tracking sensor 525 can send a signal to the electronics 520 to adjust the position, size, or orientation of the visual target to re-center or re-focus the patient's non-operative eye. This can beneficially keep the patient's non-operative eye open, centered, and focused during the eye surgery.

In some examples, the eye-tracking sensor 525 can comprise a camera that uses an image-processing algorithm to determine the orientation of the patient's non-operative eye. However, any other suitable device or algorithm can be used as the eye-tracking sensor 525.

In the illustrated example, the eye-tracking sensor 525 can be disposed on a lateral interior surface of the housing component 405 such that the eye-tracking sensor 525 does not block the patient's line-of-sight with the display screen 515 but still has a line-of-sight of the patient's non-operative eye. In other examples, the eye-tracking sensor 525 can be disposed on, behind, or even inside the display screen 515. In some examples, the eye-tracking sensor 525 can be an integrated part of the display screen 515.

Figure 6:
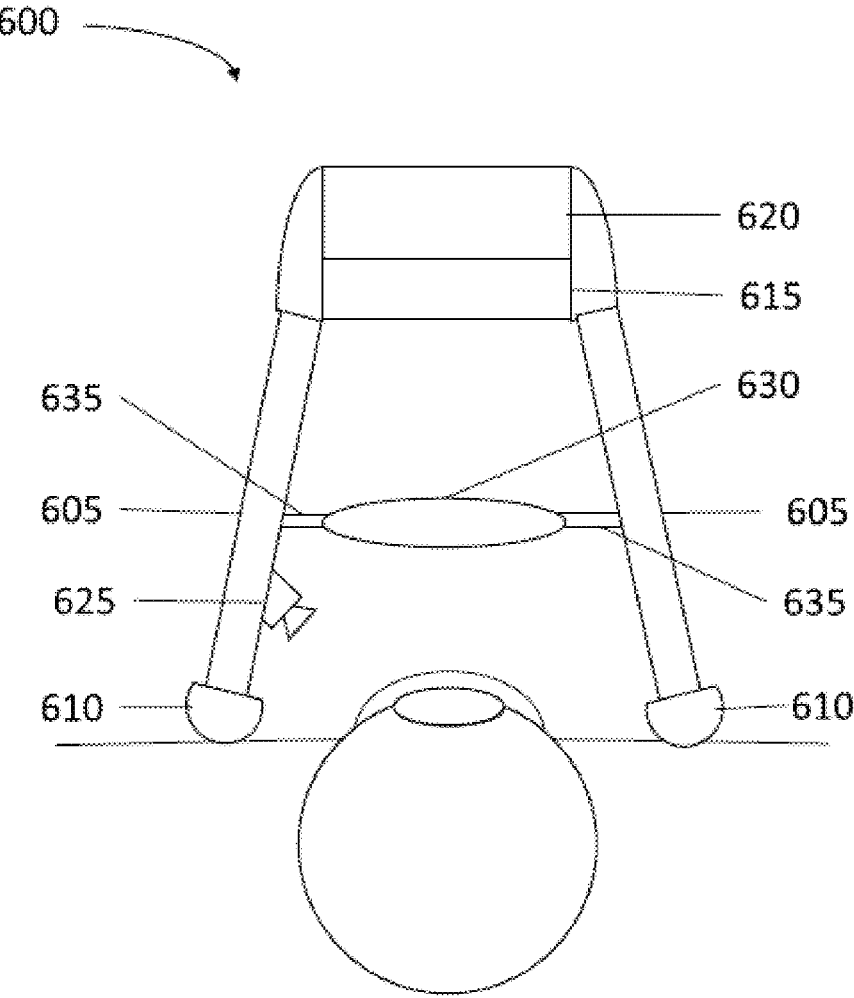
FIG. 6 depicts a cross-section view of a closed-frame visual target stimulation device, according to second example.

FIG. 6 illustrates a cross-section of an exemplary visual target stimulation device 600 placed over the patient's non-operative eye, according to another example. The visual target stimulation device 600 can comprise a housing component 605, one or more rests 610, a display screen 615, electronics 620, an eye-tracking sensor 625, and a lens 630.

The lens 630 can help focus or adjust the visual target generated by the display screen 615. The lens 630 can be disposed between the display screen 615 and the patient's non-operative eye. The lens 630 can be secured to the housing component 605. In some examples, the housing component 605 can additionally comprise a flange 635 extending along a portion of an interior circumference of the housing component 605. The flange 635 can form an opening or oculus configured to fit the lens 630. In some examples, the lens 630 can be centered beneath the display screen 615.

Figure 7:
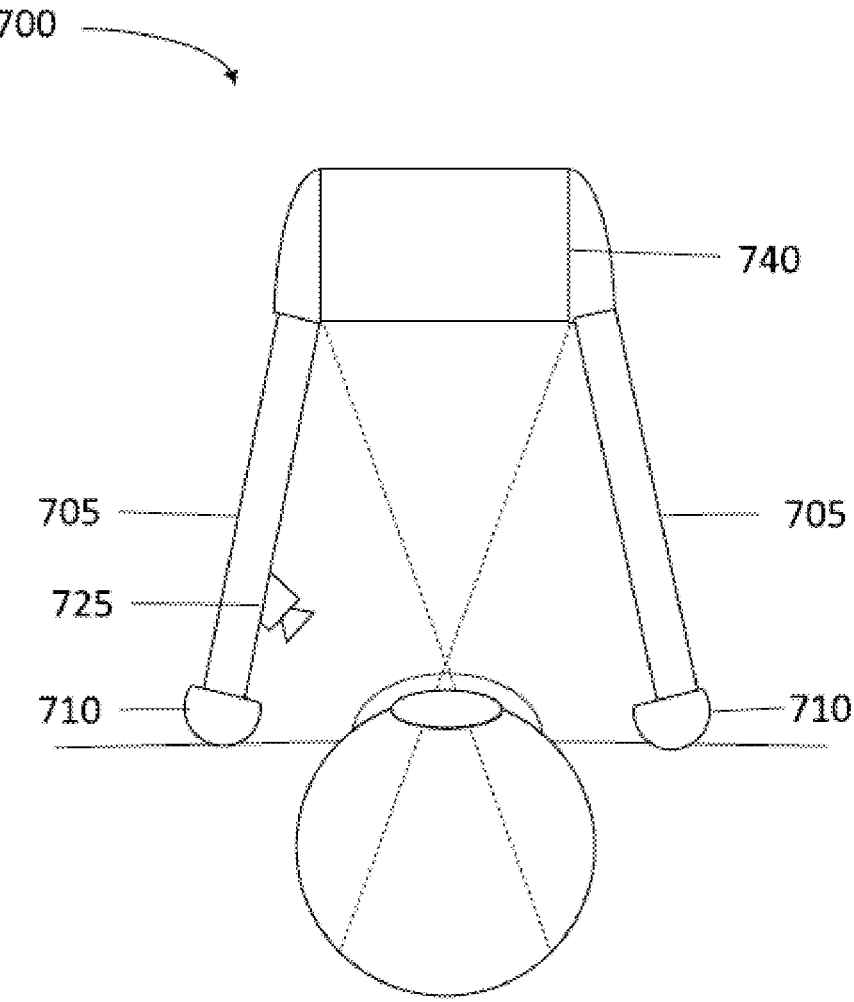
FIG. 7 depicts a cross-section view of a closed-frame visual target stimulation device, according to a third example.

FIG. 7 illustrates the exemplary visual target stimulation device 700, according to another example. In some examples, the visual target stimulation device 700 can be similar in function or structure to those depicted in FIGS. 4A-4B or FIG. 5.

The visual target stimulation device 700 can comprise a housing component 705, a rest 710, an eye-tracking sensor 725, and a retinal projector 740. However, other examples of the visual target stimulation device 700 can comprise additional or alternative components.

The retinal projector 740, which can alternatively be referred to as a virtual retina display or a retinal scan display, can project the visual target directly onto a retina of the patient's non-operative eye. This beneficially allows a patient to perceive the visual target as a hologram floating in space.

Figure 8:
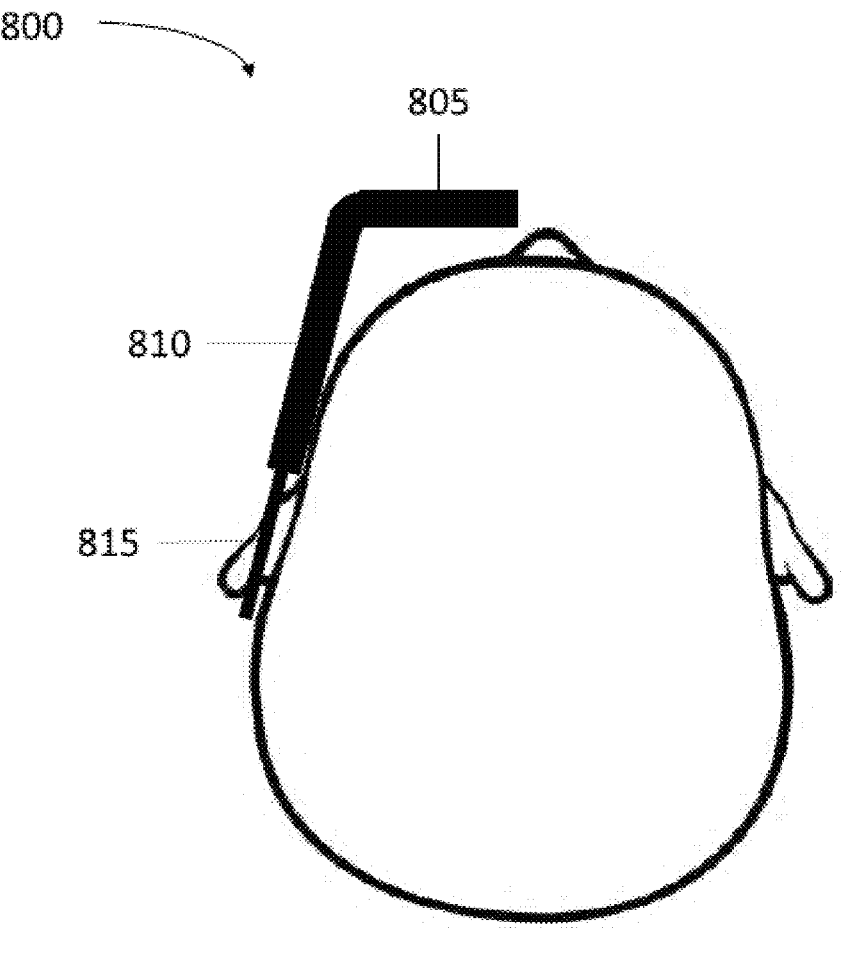
FIG. 8 depicts an overhead view of a smartglass visual target stimulation device with, according to one example.

FIG. 8 illustrates an overhead view of a visual target stimulation device 500, according to one example. In the illustrated example, the visual target stimulation device 500 can comprise a smartglass display 805 electronics 810. However, other example of the visual target stimulation device 800 can comprise additional or alternative components.

The smartglass display 805, which can alternatively be referred to as a smartglass, a display screen, a display, or a heads-up display ("HUD"), can show, project, or display the visual target to the patient. The visual target can be a static image, a video, a hologram, or any other projection on which the patient's non-operative eye can focus.

In some examples, the smartglass display 805 can be part of an augmented reality ("AR") headset, virtual reality ("VR") headset, or other wearable device.

The smartglass display 805 can be configured to only cover the non-operative eye. This beneficially allows for eye surgery to be performed on the operative eye without interference from the smartglass display 805. In some examples, the smartglass display 805 can be configured to interchangeably cover either the left eye or the right eye of the patient.

In some examples, the smartglass display 805 can comprise a visual target projector and a housing. The visual target projector can show, project, or display the visual target. The housing can partially or completely shield the patient's non-operative eye, thereby preventing ambient light from diverting the patient's attention from the visual target or from foreign objects from entering the non-operative eye.

In some examples, the smartglass display 805 can further comprise an eye-tracking sensor to detect a movement of the patient's non-operative eye. The eye-tracking sensor can additionally or alternatively determine whether the patient's non-operative eye is focused and/or centered on the visual target. In some examples, the eye-tracking sensor can have a similar function and structure as the eye-tracking sensor 425 disclosed in FIGS. 4B, the eye-tracking sensor 525 depicted in FIG. 6, or the eye-tracking sensor 725 depicted in FIG. 7.

In some examples, the eye-tracking sensor on the smartglass display 805 can determine whether the patient's non-operative eye is open, centered, or focused. If the smartglass display 805 determines that the patient's non-operative eye is not open, centered, or focused, the smartglass display 805 or another component of the visual target stimulation device 800 can adjust the visual target to re-center or re-focus the patient's non-operative eye. In some examples, the visual target stimulation device 800 can be physically adjusted. In other examples, the visual target stimulation device 800 can digitally adjust the perceived size, position, or orientation of the projected visual target.

The electronics 810 can include any components needed to operate the visual target stimulation device 800. In some examples, the electronics 810 can comprise power elements, such as a battery, a charging cable, or a power port, wherein the power elements supply electrical power to the visual target stimulation device 800.

In some examples, the electronics 810 can be adjacent the smartglass display 805. For example, if the visual target stimulation device 800 comprises a wearable headset or glasses, the electronics 510 can be stored in an arm or in a temple portion of the device 800 extending from the smartglass display 805.

In some examples, the arm or the temple portion can be configured to extend from a lateral side of the smartglass display 805. In some examples, the arm or temple portion can be configured to interchangeably extend from either lateral side of the visual target stimulation device 800. This can beneficially allow the visual target stimulation device 800 to be configured to fit over either the left eye or the right eye.

In some examples, the electronics 810 can comprise control elements such as a switch, a keypad, a dial, or a button to control the projection of the visual target. These control elements can allow the visual target stimulation device 800 to receive input for controlling the smartglass display 805.

In some examples, the electronics 810 can further comprise a computer, processor, or controller capable of controlling the smartglass display 805 and/or the earpiece 815. The electronics 810 can further comprise a memory to store instructions for operating the visual target stimulation device 800 or data collected by the visual target stimulation device 800. In some examples, the memory can comprise instructions or data for displaying the visual target. For example, if the visual target comprises a video, television program, or movie, the visual target can be stored in the memory.

The electronics 810 can further comprise a wireless transceiver, such as a Wi-Fi or Bluetooth transceiver, that allows the visual target stimulation device 800 to communicate with an outside device, such as a computer, a server, or other external hardware. The Wi-Fi or Bluetooth connection can beneficially enable the visual target stimulation device 800 to outsource one or more computing operations to a piece of external hardware, thereby reducing the size and/or complexity of the visual target stimulation device 800. In other examples, the electronics 810 comprises a wired port, including but not limited to a USB port, that allows the visual target stimulation device 800 to transmit data over a wired connection.

In some examples, instructions or data encoding the visual target can be streamed over the Wi-Fi, Bluetooth, or other wireless or wired connection to the visual target stimulation device 800. For example, if the visual target comprises a video, television program, or movie, the visual target can be streamed over the wireless connection to be projected by the smartglass display 805.

In some examples, the visual target stimulation device 800 can further comprise an earpiece 815. The earpiece 815 can help secure the visual target stimulation device 800 to the patient. Additionally or alternatively, the earpiece 815 can project audio to accompany the visual target. In these examples, the earpiece 515 can comprise an audio speaker or an earbud to project the audio. In these examples, the audio can be synched with the visual target and play while the visual target is being projected by the smartglass display

805. The earpiece 815 can further comprise controls for adjusting the volume of the audio or for selecting which audio to play.

Figure 9:
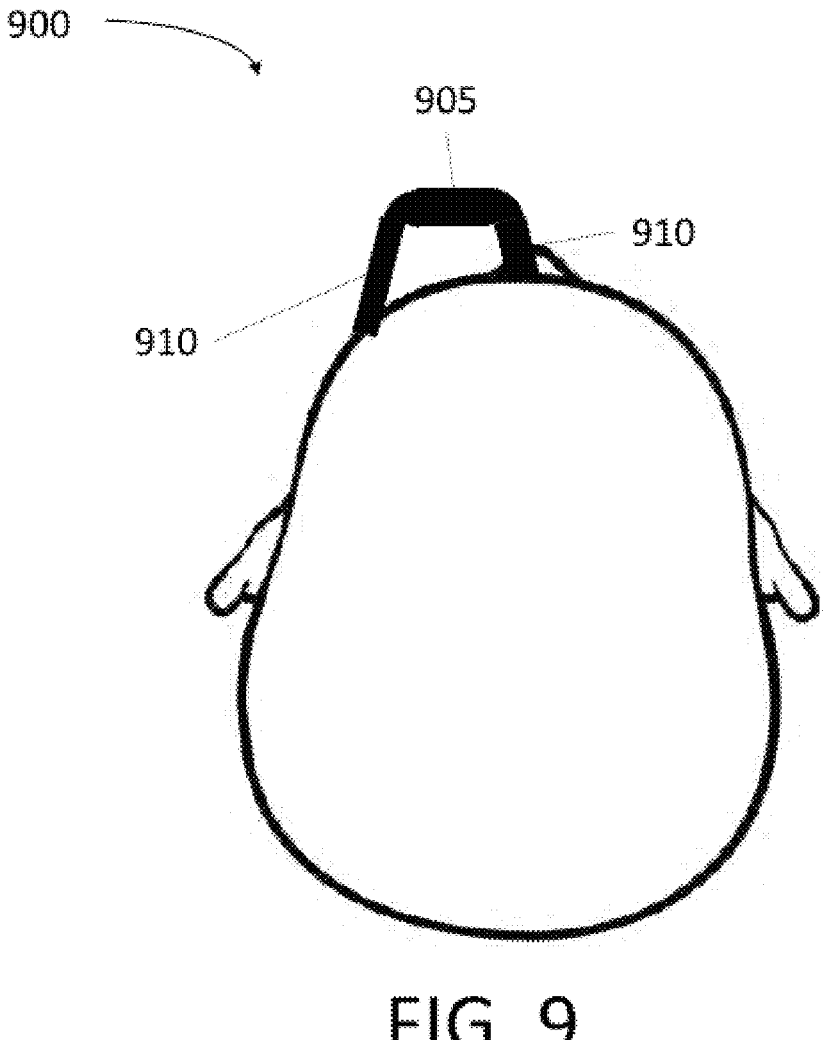
FIG. 9 depicts an overhead view of a smartglass visual target stimulation device, according to another example.

FIG. 9 illustrates a top-down view of an exemplary visual target stimulation device 900 secured to a patient's non-operative eye, according to another example. The visual target stimulation device 900 can comprise a display 905 and one or more attachments 910. However, other examples of the visual target stimulation device 900 can comprise additional or alternative components.

The attachments 910 help secure the visual target stimulation device 900 to the patient's face. Furthermore, the attachments 910 can beneficially block ambient light from saturating the visual target and from diverting the patient's focus from the visual target.

In the illustrated example, the visual target stimulation device 900 comprises two attachments 910, wherein each attachment 910 extends from a lateral side of the display 905 towards the patient's face. However, in other examples, the attachments 910 can extend from other surfaces of the display 905, such as a top surface or a bottom surface.

Figure 10:
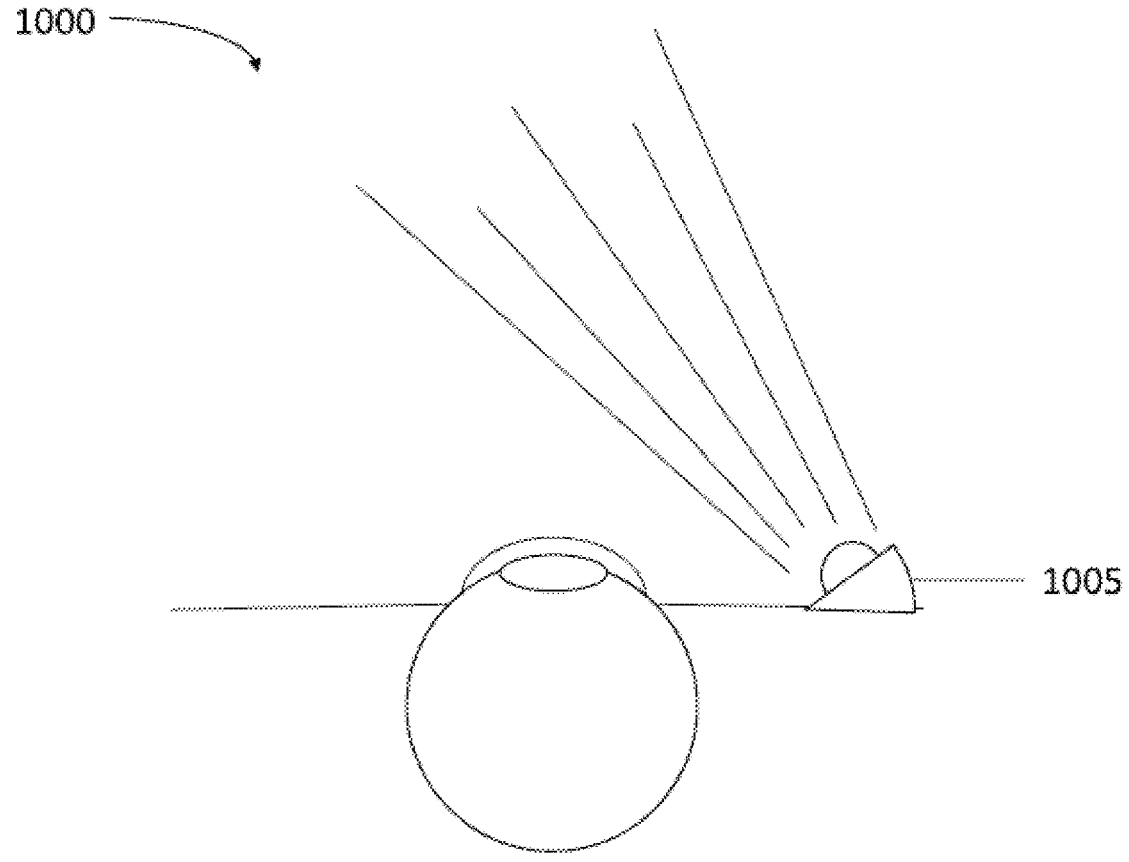
FIG. 10 depicts a holographic visual target stimulation device, according to one example.

FIG. 10 illustrates a visual target stimulation device 1000, according to another example. The visual target stimulation device 1000 can comprise a holographic projector 1005. However, other examples of the visual target stimulation device 1000 can comprise additional or alternative components.

The holographic projector 1005 can project a holographic visual target in front of the patient's non-operative eye. Projecting the visual target as a hologram can beneficially reduce the amount of physical hardware that contacts the patient's face during the eye surgery.

In some examples, the holographic projector 1005 can be secured to a portion of the patient's face adjacent the non-operative eye. In some examples, the holographic projector is secured to the temple of the patient closest to the non-operative eye (i.e., the ipsilateral temple). In some examples, the holographic projector 1005 can be secured to the patient's temple using adhesive or tape.

In some examples, the holographic projector 1005 can further comprise control elements for controlling the holographic projector 1005. These control elements can include, but are not limited to, buttons, dials, switches, keypads, touchpads, microcontrollers, processors, computers, Wi-Fi transceivers, Bluetooth transceivers, wired connections, or any other suitable means for sending instructions or commands to the holographic projector 1005.

In some examples, the holographic projector 1005 can further comprise power elements for supplying power to the holographic projector 1005. The power elements can comprise batteries, power cords, charging ports, or any other suitable means for providing power to the holographic projector 1005.

In some examples, the visual target stimulation device 1000 can further comprise a mount for the holographic projector 1005. The mount, not pictured, can comprise a monocular frame or a glasses frame that secures the holographic projector 1005 to the patient's temple, ear, face, or head. The mount can comprise any other suitable design or configuration for securing the holographic projector 1005.

In some examples, the mount can comprise an earpiece. The earpiece, not pictured in FIG. 10, can extend from the holographic projector 1005. In some examples, the earpiece can secure the holographic projector 1005 to the patient's head. In some examples, the earpiece can secure the holographic projector 1005 to an ipsilateral ear adjacent the non-operative eye.

In some examples, the earpiece can comprise an audio speaker or an earbud to project audio output. In these examples, the audio output can be synched with the visual target and play while the visual target is being projected by the holographic projector 1005. The earpiece can further comprise controls, such as volume or mute buttons, for adjusting the volume of the audio output.

As described above, the visual target stimulation devices disclosed herein can provide some stimulation to the eye to help maintain a non-operative eye in a desired position (e.g., steady, open, and forward-facing during surgery).

On rare occasion, surgeons operate on the incorrect eye. Wrong-site surgery is a devasting and preventable complication. Accordingly, there exists a need to reduce the chance of wrong-site surgery.

On rare occasion, surgeons accidently press their fingers, hand, or wrist onto the non-operative eye while operating on the operative eye. This blunt force can cause trauma to the non-operative eye, especially if the patient is under anesthesia and unable to provide feedback. Accordingly, there exists a need to reduce the chance of blunt-force trauma to the non-operative eye.

Although the present invention has been described above in some detail with reference to certain versions thereof, other versions are possible. The structural components of the invention may be of any suitable shape, dimension, material and/or configuration. While the description above refers to particular embodiments of the present invention, it will be understood that many modifications may be made without departing from the spirit thereof. The presently disclosed embodiments are therefore to be considered in all respects as illustrative and not restrictive.

Additional Examples of the Disclosed Technology

In view of the above-described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A method for performing eye surgery on an operative eye, comprising:
　securing a monocular device over a non-operative eye of an eye surgery patient, wherein the monocular device comprises:
　a frame configured to be placed on a portion of a face of the patient surrounding the non-operative eye; and
　a visual target projector coupled to the frame and disposed over the non-operative eye, wherein the visual target projector is configured to generate a visual target on which the non-operative eye can focus during the eye surgery,
　wherein the monocular device does not cover the operative eye of the patient; and
　activating the visual target projector to generate the visual target.

Example 2. The method of any of the above examples, further comprising:
　detecting a movement of the patient's non-operative eye; and
　determining, based on the movement, that the non-operative eye is no longer focused on the visual target.

Example 3. The method of any of the above examples, further comprising:

calibrating the visual target projector such that the non-operative eye is focused on the visual target.

Example 4. The method of any of the above examples, further comprising:

adjusting the visual target projector to change the position of the visual target.

Example 5. A visual target stimulation device comprising:

a visual target projector disposed above a non-operative eye of an eye surgery patient, wherein the visual target projector is configured to project a visual target towards the non-operative eye;

a lower frame portion disposed between the visual target projector and the non-operative eye, wherein the lower frame portion contacts a portion of the eye surgery patient's face adjacent the non-operative eye; and an upper frame portion connecting the visual target projector and the lower frame portion, wherein the upper frame portion comprises a plurality of wires, and wherein each wire extends from an edge portion of the lower frame portion to the visual target projector.

Example 6. The visual target stimulation device of any of the above examples, wherein the visual target stimulation device further comprises an eye shield disposed between the non-operative eye and the visual target projector, wherein the eye shield comprises a plate and a plurality of apertures through the plate.

Example 7. The visual target stimulation device of any of the above examples, wherein the eye shield is coupled to the lower frame portion.

Example 8. The visual target stimulation device of any of the above examples, wherein the visual target stimulation device further comprises a cheek rest extending from the lower frame portion toward an ipsilateral cheek of the patient.

Example 9. The visual target stimulation device of any of the above examples, wherein the visual target stimulation device further comprises a forehead rest extending from the lower frame portion toward a forehead of the patient.

Example 10. A visual target stimulation device comprising:

a dome-shaped housing configured to cover a non-operative eye of an eye surgery patient, wherein the dome-shaped housing comprises an open end and an interior surface opposite the open end;

a visual target projector mounted to the interior surface opposite the open end and disposed over the non-operative eye, wherein the visual target projector is configured to display a visual target for the non-operative eye to focus on during the eye surgery, wherein the visual target is configured to minimize movement of the non-operative eye during the eye surgery.

Example 11. The visual target stimulation device of any of the above examples, wherein the visual target projector comprises a display screen.

Example 12. The visual target stimulation device of any of the above examples, wherein the device further comprises a wireless transceiver, wherein information for displaying the visual target is streamed over the wireless transceiver.

Example 13. The visual target stimulation device of any of the above examples, wherein the device further comprises a lens coupled to the dome-shaped housing, wherein the lens is disposed between the visual target projector and the non-operative eye.

Example 14. The visual target stimulation device of any of the above examples, wherein the visual target projector comprises a retinal projector and wherein the visual target is projected onto a retina of the non-operative eye.

Example 15. The visual target stimulation device of any of the above examples, wherein the visual target stimulation device further comprises an eye-tracking sensor coupled to the housing, wherein the eye-tracking sensor tracks the position of the non-operative eye.

Example 16. The visual target stimulation device of any of the above examples, wherein the device further comprises an earpiece extending from the housing, wherein the earpiece is configured to be secured to an ipsilateral ear of the patient.

Example 17. The visual target stimulation device of any of the above examples, wherein the earpiece further comprises an audio speaker configured to generate audio synched with the visual target.

Example 18. A visual target stimulation device comprising:

a holographic projector adjacent a non-operative eye of an eye surgery patient, wherein the holographic projector is configured to generate a visual target for the non-operative eye to focus on during an eye surgery.

Example 19. The visual target stimulation device of any of the above examples, wherein the holographic projector is secured to an ipsilateral temple of an eye surgery patient.

Example 20. The visual target stimulation device of any of the above examples, wherein the device further comprises an earpiece connected to the holographic projector, wherein the earpiece is configured to secure the device to an ipsilateral ear of an eye surgery patient.

I claim:

1. A method for performing eye surgery on an operative eye, comprising:

securing a monocular device over a non-operative eye of an eye surgery patient, wherein the monocular device comprises:

a frame configured to be placed on a portion of a face of the patient surrounding the non-operative eye; and a visual target projector coupled to the frame and disposed over the non-operative eye, wherein the visual target projector is configured to generate a visual target on which the non-operative eye can focus during the eye surgery, wherein the monocular device does not cover the operative eye of the patient; activating the visual target projector to generate the visual target;

detecting a movement of the patient's non-operative eye; and determining, based on the movement, that the non-operative eye is no longer focused on the visual target.

2. The method of claim 1, further comprising:

calibrating the visual target projector such that the non-operative eye is focused on the visual target.

3. The method of claim 1, further comprising:

adjusting the visual target projector to change the position of the visual target.

4. A monocular visual target stimulation device for use by a patient comprising:

a visual target projector a frame that contacts a portion of a face of the patient and that supports the visual target projector in an orientation above one eye of the patient, wherein the visual target projector is configured to project a visual target towards the one eye of the patient to stimulate the one eye of the patient but not another eye of the patient, wherein the visual target stimulation device further comprises an eye shield disposed between the one eye and the visual target projector, wherein the eye shield comprises a plate and a plurality of apertures through the plate.

5. The visual target stimulation device of claim 4, wherein the eye shield is coupled to the frame.

6. The visual target stimulation device of claim 4, wherein the visual target stimulation device further comprises a cheek rest extending from the frame toward an ipsilateral cheek of the patient.

7. The visual target stimulation device of claim 4, wherein the visual target stimulation device further comprises a forehead rest extending from the frame toward a forehead of the patient.

8. A visual target stimulation device comprising:
a dome-shaped housing configured to cover a non-operative eye of an eye surgery patient, wherein the dome-shaped housing comprises an open end and an interior surface opposite the open end;
a visual target projector mounted to the interior surface opposite the open end and disposed over the non-operative eye, wherein the visual target projector is configured to display a visual target for the non-operative eye to focus on during the eye surgery,
wherein the device further comprises a wireless transceiver, wherein information for displaying the visual target is streamed over the wireless transceiver.

9. The visual target stimulation device of claim 8, wherein the visual target projector comprises a display screen.

10. The visual target stimulation device of claim 8, wherein the device further comprises a lens coupled to the dome-shaped housing, wherein the lens is disposed between the visual target projector and the non-operative eye.

11. The visual target stimulation device of claim 8, wherein the visual target projector comprises a retinal projector and wherein the visual target is projected onto a retina of the non-operative eye.

12. The visual target stimulation device of claim 8, wherein the visual target stimulation device further comprises an eye-tracking sensor coupled to the housing, wherein the eye-tracking sensor tracks the position of the non-operative eye.

13. The visual target stimulation device of claim 8, wherein the device further comprises an earpiece extending from the housing, wherein the earpiece is configured to be secured to an ipsilateral ear of the patient.

14. The visual target stimulation device of claim 13, wherein the earpiece further comprises an audio speaker configured to generate audio synched with the visual target.

15. A visual target stimulation device comprising:
a dome-shaped housing configured to cover a non-operative eye of an eye surgery patient, wherein the dome-shaped housing comprises an open end and an interior surface opposite the open end;
a visual target projector mounted to the interior surface opposite the open end and disposed over the non-operative eye, wherein the visual target projector is configured to display a visual target for the non-operative eye to focus on during the eye surgery,
wherein the visual target projector comprises a retinal projector and wherein the visual target is projected onto a retina of the non-operative eye.

* * * * *